(12) United States Patent
Mottram et al.

(10) Patent No.: US 11,999,062 B2
(45) Date of Patent: Jun. 4, 2024

(54) ROBOTIC JOINT CONTROL

(71) Applicant: CMR SURGICAL LIMITED, Cambridge (GB)

(72) Inventors: Edward John Mottram, Cambridge (GB); Gordon Thomas Deane, Cambridge (GB)

(73) Assignee: CMR SURGICAL LIMITED, Cambridge (GB)

( * ) Notice: Subject to any disclaimer, the term of this patent is extended or adjusted under 35 U.S.C. 154(b) by 233 days.

(21) Appl. No.: 17/081,120

(22) Filed: Oct. 27, 2020

(65) Prior Publication Data
US 2021/0122041 A1    Apr. 29, 2021

(30) Foreign Application Priority Data
Oct. 29, 2019 (GB) ...................................... 1915687

(51) Int. Cl.
  *B25J 9/16* (2006.01)
  *A61B 34/30* (2016.01)
  *B25J 13/02* (2006.01)

(52) U.S. Cl.
  CPC .............. *B25J 9/1651* (2013.01); *A61B 34/30* (2016.02); *B25J 9/1607* (2013.01); *B25J 13/025* (2013.01); *G05B 2219/40381* (2013.01)

(58) Field of Classification Search
  CPC ...... B25J 9/1651; B25J 9/1676; B25J 9/1607; B25J 13/025; B25J 9/06; B25J 9/08;
  (Continued)

(56) References Cited

U.S. PATENT DOCUMENTS

| | | | | |
|---|---|---|---|---|
| 4,195,495 A | * | 4/1980 | Sehlbach | .................. F16D 3/40 464/117 |
| 6,192,297 B1 | * | 2/2001 | Marobin | ................ B25J 9/1666 700/165 |

(Continued)

FOREIGN PATENT DOCUMENTS

| CN | 209285723 U | 8/2019 |
|---|---|---|
| JP | S60039204 A | 3/1985 |

(Continued)

OTHER PUBLICATIONS

United Kingdom Search Report from corresponding United Kingdom Application No. GB1915687.6 dated Apr. 15, 2020.
(Continued)

*Primary Examiner* — Khoi H Tran
*Assistant Examiner* — Sarah A Tran
(74) *Attorney, Agent, or Firm* — Lando & Anastasi, LLP

(57) ABSTRACT

A method for limiting joint velocity of a plurality of joints of a surgical robotic system, the surgical robotic system comprising a robot having a base and an arm extending from the base to an attachment for an instrument, the arm comprising a plurality of joints whereby the configuration of the arm can be altered, the method comprising: obtaining joint states for a first group of k joints of the arm, where k>1; for each of the k joints: determining from the obtained joint state a permitted range of motion for that joint; deriving, using the permitted range of motion, a joint velocity limit for that joint; selecting the minimum joint velocity limit of the k joints to be a common joint velocity limit used to limit each of the k joints individually; and calculating drive signals for driving the k joints wherein the velocity of each of the k joints is limited using the common joint velocity limit.

20 Claims, 9 Drawing Sheets

(58) Field of Classification Search
CPC .............. A61B 34/76; A61B 2090/066; A61B 2090/067; A61B 2034/2059; A61B 34/30; G05B 2219/40381; G05B 2219/43201; G05B 2219/40353; G05B 2219/45118
See application file for complete search history.

(56) References Cited

U.S. PATENT DOCUMENTS

| | | | | |
|---|---|---|---|---|
| 6,424,885 | B1* | 7/2002 | Niemeyer | A61B 34/35 600/109 |
| 6,772,053 | B2* | 8/2004 | Niemeyer | A61B 1/00149 348/E13.016 |
| 9,517,561 | B2* | 12/2016 | Khripin | B25J 9/1664 |
| 9,645,565 | B2* | 5/2017 | Nilsson | B25J 9/1641 |
| 10,019,566 | B1* | 7/2018 | Gallagher | B25J 9/1666 |
| 10,029,367 | B2* | 7/2018 | Hourtash | B25J 9/1643 |
| 2007/0138992 | A1 | 6/2007 | Prisco et al. | |
| 2014/0039681 | A1 | 2/2014 | Bowling et al. | |
| 2014/0297030 | A1 | 10/2014 | Iwasaki | |
| 2017/0296277 | A1 | 10/2017 | Hourtash et al. | |

FOREIGN PATENT DOCUMENTS

| | | |
|---|---|---|
| JP | H05341834 A | 12/1993 |
| JP | 2005044230 A | 2/2005 |
| JP | 2014161918 A | 9/2014 |
| JP | 2014193519 A | 10/2014 |
| JP | 2019048084 A | 3/2019 |
| WO | 9523054 A1 | 8/1995 |
| WO | 2014146095 A1 | 9/2014 |
| WO | 2019115471 A1 | 6/2019 |
| WO | 2020028356 A1 | 2/2020 |

OTHER PUBLICATIONS

Notification of Transmittal of the International Search Report and the Written Opinion of the International Searching Authority from corresponding PCT/GB2020/052715 dated Jan. 13, 2021.
Japanese Notification of Reasons for Refusal from corresponding Japanese Application No. 2021-532491 dated Aug. 2, 2022.
Japanese Notification of Reasons for Refusal from corresponding Japanese Application No. 2021-532491 dated Feb. 14, 2023.
Japanese Decision of Grant from corresponding Japanese Application No. 2021-532491 dated May 30, 2023.

* cited by examiner

ROBOTIC JOINT CONTROL

CROSS-REFERENCE TO RELATED APPLICATION

This application claims the benefit under 35 U.S.C. § 119 of United Kingdom Patent Application No. 1915687.6 filed on Oct. 29, 2019 which is hereby incorporated herein by reference in its entirety for all purposes.

FIELD OF THE INVENTION

This invention relates to the control of joints in robotic systems such as robot arms, and in particular to limiting joint velocities of a plurality of joints by a common joint velocity limit determined from one of the joints.

BACKGROUND

A typical robotic manipulator comprises a series of rigid elements which are coupled together by joints. The elements may be joined in series to form an arm. The joints can be driven so as to cause relative motion of the rigid elements. The rigid elements may stem from a base and terminate in an attachment for an instrument or end effector. Thus motion at the joints can be used to position the end effector at a desired location. Each joint may provide rotational motion or linear motion. The joints may be driven by any suitable means, for example electric motors or hydraulic actuators.

During operation, the robot may be required to cause the end effector to move to a desired position. For example, the robot may be required to use the end effector to pick up an object. This requires the end effector to be moved to where the object is. To accomplish this, some combination of motions of the joints is required. A control system of the robot is used to calculate those motions.

Conventionally, a robot is provided with position sensors, each of which senses the configuration of a respective one of the joints. This position information is fed to the control system.

A known strategy for the control system is as follows:
1. Receive information indicating a desired position of the end effector.
2. Determine a set of target configurations of the joints of the robot that will result in the end effector being in that position. This is known as inverse kinematics.
3. Receive information indicating the current configuration of each joint in the robot, compare those current configurations to the target configurations and calculate a set of torques or forces required at each joint in order to reduce the error between the respective joint's current and target positions.
4. Send drive signals to the actuators in the robot in order to impose those torques or forces at the respective joints.

This series of steps is performed repetitively so that over time the motion of the robot conforms to the target configurations.

This approach is problematic because typically the inverse kinematics problem is considered hard to solve. One reason for this is that certain poses of the manipulator can become singular, meaning that it is impossible to make subsequent movements of the end effector in all directions with finite joint velocities.

There is a need for an improved control system for mechanical systems such as robot manipulators.

SUMMARY

This summary is provided to introduce a selection of concepts that are further described below in the detailed description. This summary is not intended to identify key features or essential features of the claimed subject matter, nor is it intended to be used to limit the scope of the claimed subject matter.

According to an aspect of the present invention there is provided a method for limiting joint velocity of a plurality of joints of a surgical robotic system, the surgical robotic system comprising a robot having a base and an arm extending from the base to an attachment for an instrument, the arm comprising a plurality of joints whereby the configuration of the arm can be altered, the method comprising:
  obtaining joint states for a first group of k joints of the arm, where k>1;
  for each of the k joints:
    determining from the obtained joint state a permitted range of motion for that joint;
    deriving, using the permitted range of motion, a joint velocity limit for that joint;
  selecting the minimum joint velocity limit of the k joints to be a common joint velocity limit used to limit each of the k joints individually; and
  calculating drive signals for driving the k joints wherein the velocity of each of the k joints is limited using the common joint velocity limit.

According to another aspect of the present invention there is provided a method for limiting joint velocity of a plurality of joints of a surgical robotic system, the surgical robotic system comprising a robot having a base and an arm extending from the base to an attachment for an instrument, the arm comprising a plurality of joints whereby the configuration of the arm can be altered, the method comprising:
  obtaining joint states for a first group of k joints of the arm, where k>1;
  for each of the k joints, determining from the obtained joint state a permitted range of motion for that joint;
  deriving, using the minimum permitted range of motion of the k joints and the joint to which that minimum permitted range of motion pertains, a common joint velocity limit used to limit each of the k joints individually; and
  calculating drive signals for driving the k joints wherein the velocity of each of the k joints is limited using the common joint velocity limit.

The following may relate to one or more of the aspects herein.

The first group of k joints may comprise k joints proximal to the base of the arm, and the common joint velocity limit may limit the positional velocity of the kth joint along orthogonal directions in Cartesian space. The first group of k joints may comprise k joints proximal to the base of the arm, and the k joints may enable a position of a (k+m)th joint to be uniquely determined, where m>0. The common joint velocity limit may limit the positional velocity of a (k+m)th joint along orthogonal directions in Cartesian space. The velocity of each of the k joints individually may be limited to the common joint velocity limit.

The arm may comprise n joints, where n>k, and the method may comprises: obtaining joint states for a second group of (n−k) joints of the arm; for each of the (n−k) joints: determining from the obtained joint state a permitted range of motion for that joint; deriving, using the permitted range of motion, a joint velocity limit for that joint; selecting the minimum joint velocity limit of the (n−k) joints to be a further common joint velocity limit for each of the (n–k) joints individually; and calculating drive signals for driving the (n–k) joints wherein the velocity of each of the (n–k) joints is limited to the further common joint velocity limit.

Obtaining joint states for one or both of the first group of k joints and the second group of (n–k) joints may comprise obtaining joint angles. Determining the permitted range of motion of a joint may comprise determining a closest angular distance to a joint angular limit for that joint. Deriving the joint velocity limit may comprise using a maximum deceleration for the respective joint and the determined closest angular distance to the joint angular limit. The further common joint velocity limit may limit the angular velocity of a (k+m)th joint, where m>0. The further common joint velocity limit may limit the angular velocity of the nth joint.

At least one of the joint angular limit for a joint and the maximum deceleration for a joint may comprise a predetermined value. At least one of the joint angular limit for a joint and the maximum deceleration for a joint may be determined from a physical characteristic of the joint. At least one of the joint angular limit for a joint and the maximum deceleration for a joint may be user-definable. Where the determined closest angular distance to the joint angular limit exceeds a threshold angular distance, the joint velocity limit for that joint may comprise a predetermined joint velocity limit value. The predetermined joint velocity limit value may be user-definable.

Deriving the joint velocity limit may comprise translating joint angular positions and/or velocities into positions and/or velocities, respectively, in Cartesian space. The translating may comprise determining a Jacobian matrix. The translating may comprise using the determined Jacobian matrix to derive an inverse matrix. The translating may comprise determining a Euclidean norm in respect of each row of the inverse matrix.

The method may comprise providing feedback to a user of the surgical robotic system based on a commanded joint velocity for a joint exceeding the common joint velocity limit or further common joint velocity limit for that joint. The surgical robotic system may comprise an input controller manipulatable by a user thereby to alter the configuration of the arm, and the method may comprise providing haptic feedback via the input controller. The haptic feedback may comprise applying a resistive force to movement of the input controller.

According to another aspect of the present invention there is provided a joint velocity limiting system for limiting joint velocity of a plurality of joints of a surgical robotic system, the surgical robotic system comprising a robot having a base and an arm extending from the base to an attachment for an instrument, the arm comprising a plurality of joints whereby the configuration of the arm can be altered, the joint velocity limiting system being configured to:
   obtain joint states for a first group of k joints of the arm, where k>1;
   for each of the k joints:
      determine from the obtained joint state a permitted range of motion for that joint;
      derive, using the permitted range of motion, a joint velocity limit for that joint;
   select the minimum joint velocity limit of the k joints to be a common joint velocity limit used to limit each of the k joints individually; and
   calculate drive signals for driving the k joints wherein the velocity of each of the k joints is limited using the common joint velocity limit.

According to another aspect of the present invention there is provided a joint velocity limiting system for limiting joint velocity of a plurality of joints of a surgical robotic system, the surgical robotic system comprising a robot having a base and an arm extending from the base to an attachment for an instrument, the arm comprising a plurality of joints whereby the configuration of the arm can be altered, the joint velocity limiting system being configured to:
   obtain joint states for a first group of k joints of the arm, where k>1;
   for each of the k joints determine from the obtained joint state a permitted range of motion for that joint;
   derive, using the minimum permitted range of motion of the k joints and the joint to which that minimum permitted range of motion pertains, a common joint velocity limit used to limit each of the k joints individually; and
   calculate drive signals for driving the k joints wherein the velocity of each of the k joints is limited using the common joint velocity limit.

According to another aspect of the present invention there is provided a joint velocity limiting system for a surgical robotic system configured to perform the method as described herein.

According to another aspect of the present invention there is provided a surgical robotic system comprising a robot having a base and an arm extending from the base to an attachment for an instrument, and a joint velocity limiting system configured for limiting joint velocities by the method as described herein.

According to another aspect of the present invention there is provided a non-transitory computer readable storage medium having stored thereon computer readable instructions that, when executed at a computer system, cause the computer system to perform the method as described herein.

Any feature of any aspect described herein may be combined with any other feature of any aspect described herein. Any apparatus feature may be rewritten as a method feature, and vice versa. These are not written out in full merely for the sake of brevity.

BRIEF DESCRIPTION OF THE DRAWINGS

The present invention will now be described by way of example with reference to the accompanying drawings.
   In the drawings.

DETAILED DESCRIPTION

Figure 1:
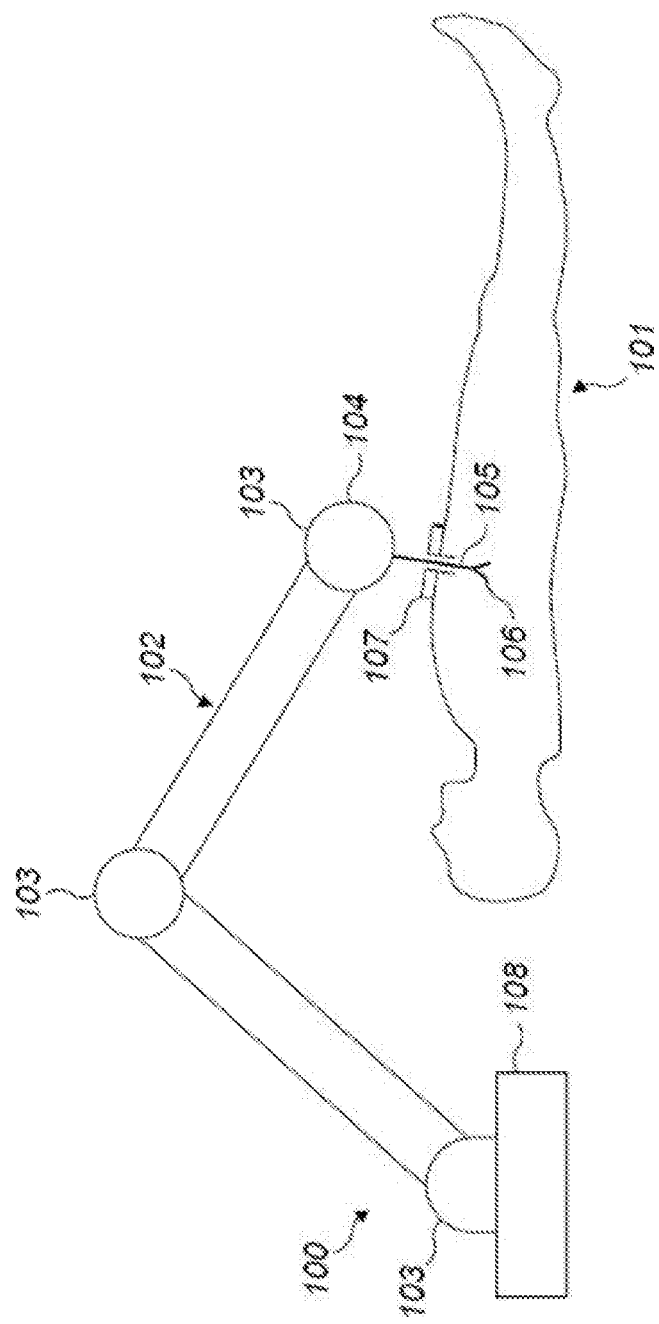
FIG. 1 illustrates a typical surgical robot.

The following description is presented by way of example to enable a person skilled in the art to make and use the invention. The present invention is not limited to the embodiments described herein and various modifications to the disclosed embodiments will be apparent to those skilled in the art. Embodiments are described by way of example only.

A robot arm such as a surgical robot arm can be controlled to move in response to one or more drive signals. The drive signals effect motion of one or more joints of the arm. The robot arm is moved in accordance with a commanded movement of the arm, for example in accordance with an input received at an input controller coupled to the robot arm. The velocity of motion of joints of the arm corresponds to the velocity of motion of the input controller. Generally, as the input controller is moved more quickly, joints of the arm are driven to move more quickly.

The joints of the arm have a limited maximum torque. Thus situations can arise in which the movement of the arm cannot keep up with the commanded movement. Rather than the robot arm control system attempting to drive joints at high speeds to keep up with the commanded movement, it is appropriate to apply a velocity limit to the joints. This can help ensure that the joints are not moving so fast that they cannot be controlled to stop smoothly by their respective joint angular limits. Suitably, a common velocity limit can be determined from a subset of joints of the arm, for example a single joint, and applied to or used to limit the velocity of more than one joint of the arm. In some cases the common joint velocity limit can be applied to joints individually. The common joint velocity can be applied to all of the joints of the arm.

Determining a suitable joint velocity limit for each joint dynamically and on the basis of the commanded movement can be computationally intensive, and requires knowledge of the commanded joint movements. A more efficient approach, as described herein, is to calculate a joint velocity limit as a function of the pose of the arm. The joint velocity limit is suitably calculated based on the joints of the arm, e.g. on characteristics of the joints such as angular rotational limits of the joints and/or maximum joint decelerations of the joints. The present approach enables the joint velocity limit to be calculated at lower processing power and/or potentially more quickly, which can improve the efficiency of the control system. The present approach permits limiting the velocity of joints of the arm without needing to know the commanded movements, e.g. without needing access to an input received from the input controller. The present approach can recognise when a given pose would result, or would be likely to result, in rapid motion of one or more joints of the arm and can anticipate such rapid motion by limiting a plurality of joints of the arm in response.

As described in more detail below, the velocity of multiple joints of a robot arm, such as a surgical robot arm, can be limited by obtaining joint states (such as joint angles) for multiple joints of the arm. For each of these multiple joints, a permitted range of motion is determined. This can include calculating how far the joint can move or rotate in either direction from its current position. A joint velocity limit for each of the multiple joints is then derived. This derivation can be based on a maximum deceleration of the respective joint, to ensure that the joint can come to a stop at a rotational limit of the joint, e.g. the rotational limit closest to the current angular position. The lowest of the derived joint velocity limits is selected as a common joint velocity limit, which can be applied to each of the multiple joints individually. The common joint velocity limit can be used to limit each of the multiple joints individually. Drive signals for driving the multiple joints are calculated, and can limit the velocity of each of the multiple joints to the common joint velocity limit.

Setting the minimum joint velocity limit of the joints as the common joint velocity limit for all of the joints can ensure that none of the joints will exceed their respective joint velocity limits. Motion of a portion of the arm distal of the multiple joints will depend on motion of each of the joints individually. By setting the common joint velocity limit for each of these joints individually, the velocity of that distal portion of the arm can also be limited in a convenient manner. The common joint velocity limit can be applied to the portion of the arm distal of the multiple joints, for example a next joint from the multiple joints, or a more distal joint from the multiple joints. The common joint velocity limit can be applied so as to limit the velocity at which the position of that portion of the arm can move (e.g. positional velocity along the three orthogonal axes of Cartesian space). The velocity of that portion of the arm will depend on the velocity of the multiple joints, i.e. joints more proximal to the base of the arm than that portion of the arm. Thus applying the common joint velocity limit to that portion of the arm will have the effect of limiting the velocity of the multiple joints. The velocity of the multiple joints may, individually, be limited to the common joint velocity limit. Where more than one of the multiple joints move at once, it is likely that the maximum velocity of those joints will be less than the common joint velocity limit.

A robot arm may be kinematically redundant, or simply 'redundant', in that there are multiple configurations of joints of the arm which result in the same spatial relationship between a base of the arm and an attachment for an instrument at an end of the arm distal from the base of the arm. A redundant arm is able to perform a given task and move (including orient) an instrument or endoscope (attached to the arm) to a desired position with more than one possible arm configuration or "pose".

Such redundancy can give flexibility in the configuration of the arm, but can also lead to problems: some arm configurations may be less desirable than others. This can be because the arm is more likely to collide with another object or a person in the workspace in one configuration than in another configuration. A configuration may be undesirable because it limits subsequent movement, for example of a joint or of the end effector. For example, a particular position of the end effector may be achievable with a given joint well within its operating range, or close to a limit of its operating range. The latter configuration is less desirable in that the given joint may reach its operating limit in a subsequent movement, potentially restricting the movement of the end effector or leading to another cause of undesirable high joint speeds at other joints to compensate for the restricted movement. The joint limit acts as a constraint on joint movement, and hence on the arm.

In the present techniques, action can be taken, e.g. by a control system, to avoid undesirable high joint speeds, whether caused by a high commanded velocity and/or by constraints on the arm causing high joint velocities to occur, or in some other way. This action can be taken based on the current joint states, or angles. E.g. knowledge of the pose of the arm, or of at least a subset of joints of the arm, can be sufficient to enable the velocities of multiple joints of the arm to be limited. Knowledge of the commanded motion is not needed.

FIG. 1 illustrates a typical surgical robot 100 for use in performing laparoscopic surgery which consists of a base 108, an arm 102, and an instrument 105. The base supports the robot, and is itself attached rigidly to, for example, the operating theatre floor, the operating theatre ceiling, a trolley or a patient bed. The arm extends between the base and the instrument. The arm is articulated by means of multiple flexible joints 103 along its length, which are used to locate the surgical instrument in a desired location (which can include orientation) relative to the patient. The surgical instrument is attached to the distal end 104 of the robot arm. The surgical instrument penetrates the body of the patient 101 at a port 107 so as to access the surgical site. At its distal end, the instrument comprises an end effector 106 for engaging in a medical procedure.

A typical robot arm will comprise a driver for each joint which is configured to drive the joint to move. A typical robot arm will comprise a joint sensor for each joint configured to sense a state of the joint.

Figure 2:
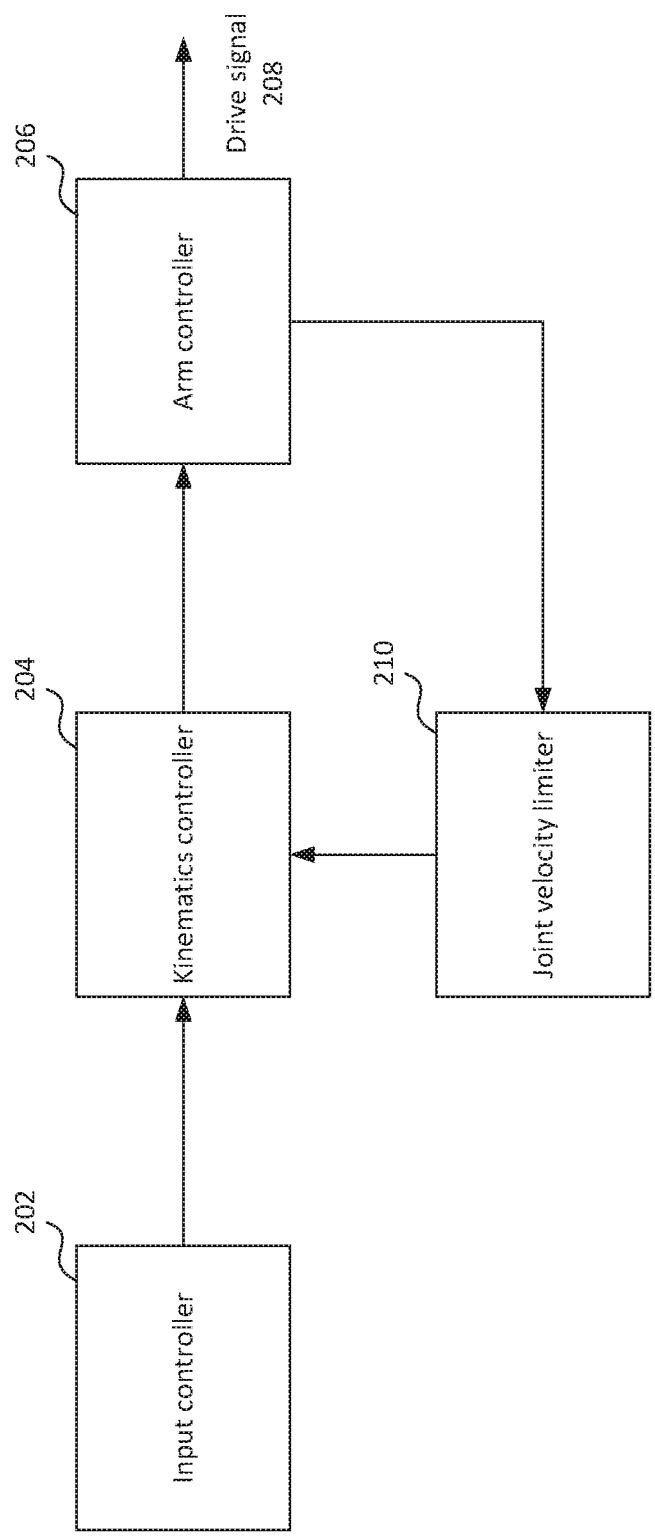
FIG. 2 illustrates a schematic of a system for controlling a robot arm.

The present approach will be described with reference to FIG. 2, illustrating a system for controlling a robot arm. The system comprises an input controller 202 coupled to a kinematics controller 204. The kinematics controller 204 is coupled to an arm controller 206 such as an arm base controller. The arm controller 206 outputs a signal 208 for driving joints of the robot arm. The arm controller is also coupled to a joint velocity limiter 210. The joint velocity limiter is coupled to the kinematics controller 204. The joint velocity limiter 210 suitably forms part of a joint velocity limiting system. The kinematics controller 204 may form part of the joint velocity limiting system. The arm controller 206 may form part of the joint velocity limiting system.

The input controller 202 is manipulatable for controlling the position of the robot arm. A user of the system, such as a surgeon, can manipulate the input controller so as to command a desired operation of the arm, including movement of the arm. An output of the input controller can be representative of a commanded pose for the robot arm. For example, the output of the input controller may comprise a desired movement of a distal joint of the robot arm. This output is received at the kinematics controller 204. The kinematics controller is configured to determine a desired pose of the robot arm in response to the commanded pose. Typically this will correspond to a desired movement of the arm towards that desired pose from the current pose. The kinematics controller outputs the desired pose to the arm controller 206 which is configured to calculate the drive signals 208 necessary for driving the joints of the arm so as to achieve the desired pose. The determination of the desired pose and/or the calculation of the drive signals necessary to achieve that desired pose can be carried out in any suitable way. For example, the desired pose of the arm, which can include desired joint angles of each of the driven joints, can be determined based on the current pose of the arm. Movements of each of the joints for causing the desired movement of the distal joint of the arm can be determined. The kinematics controller and/or the arm controller suitably have access to the current pose of the arm, for example by having access to the joint states of the arm and/or by maintaining a record, for example at a memory, of previous adjustments to the arm position, such as drive signals used to drive the arm. For example, the kinematics controller and/or the arm controller may be configured to receive signals from the joint sensors. The received signals can be indicative of the current rotational position of the respective joints.

The arm controller is configured to output joint states, for example joint angular positions, of at least a subset of the joints of the arm to the joint velocity limiter 210. The joint velocity limiter is configured to derive a common joint velocity limit for a plurality of joints of the arm in dependence on the received joint states. The common joint velocity limit is output by the joint velocity limiter to the kinematics controller. The kinematics controller can therefore determine the desired pose of the arm in dependence on the commanded pose and the common joint velocity limit for the plurality of joints of the arm. The movements of the arm controlled by the drive signals 208 can therefore take into account the current pose of the arm and a common joint velocity limit derived from that current pose.

Suitably the arm is controlled such that the position of a selected portion of the arm, for example a joint or location of the arm such as a wrist of the arm, will lie on a straight line joining a current position of that selected portion and a commanded position of that selected portion, or as close to that straight line as can be achieved whilst satisfying other control criteria. Thus, the position of the selected portion of the arm will follow a path expected by a user controlling the arm. Thus, where the velocity of a joint is restricted, the velocities of other joints are also likely to need to be modified such that the position of the selected portion of the arm follows the desired path.

Figure 3:
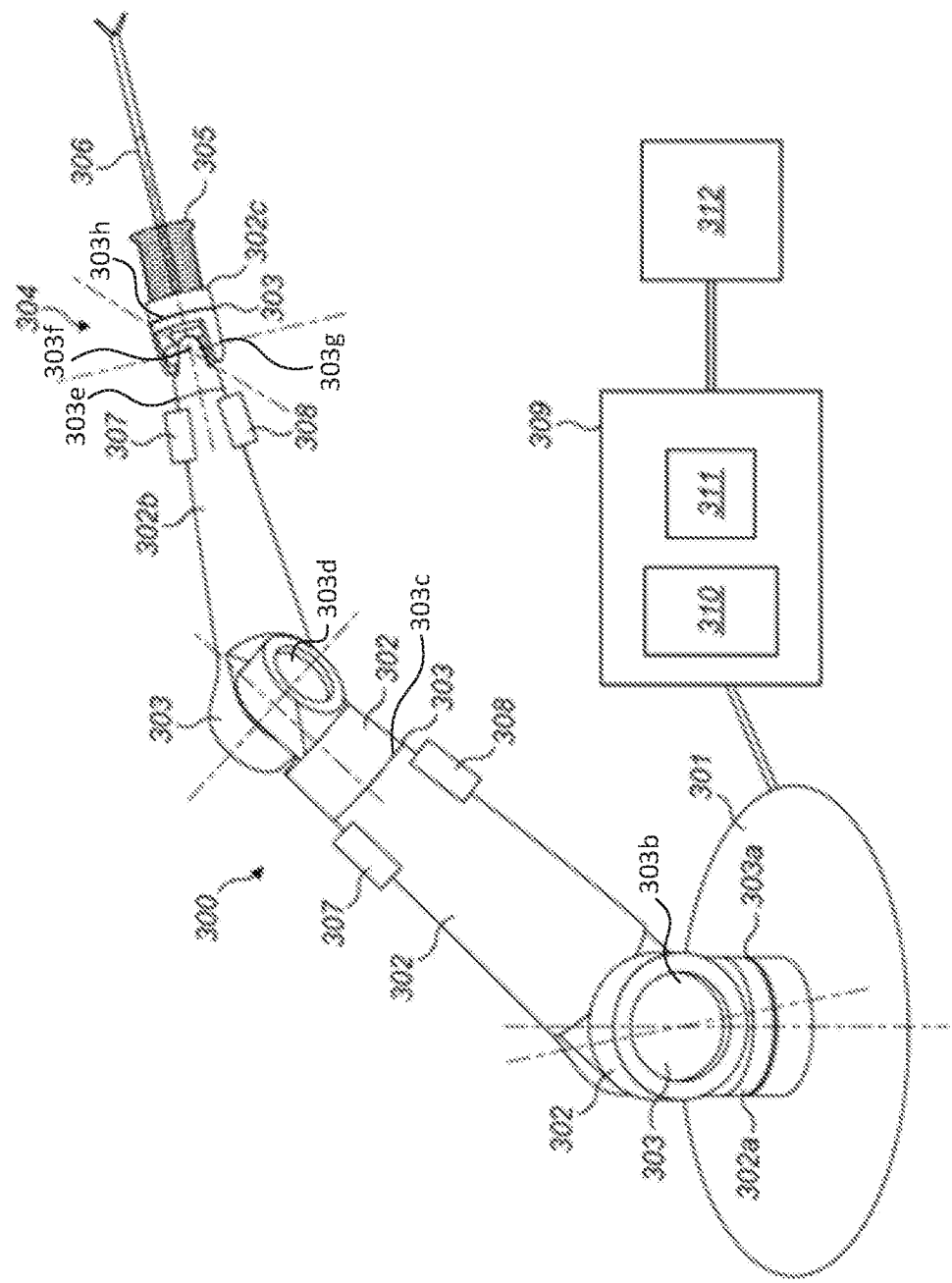
FIG. 3 illustrates another surgical robot.

The present techniques will now be described further with respect to a particular arrangement of a robot arm. FIG. 3 illustrates a surgical robot having an arm 300 which extends from a base 301. The arm comprises a number of rigid limbs 302. The limbs are coupled by revolute joints 303. The most proximal limb 302a is coupled to the base by a proximal joint 303a. It and the other limbs are coupled in series by further ones of the joints 303. Suitably, a wrist 304 is made up of four individual revolute joints. The position of the wrist can be defined as the location at which rotational axes of at least two of the revolute joints intersect. The wrist 304 couples one limb (302b) to the most distal limb (302c) of the arm. The most distal limb 302c carries an attachment 305 for a surgical instrument 306. Each joint 303 of the arm has one or more motors 307 which can be operated to cause rotational motion at the respective joint, and one or more position and/or torque sensors 308 which provide information regarding the current configuration and/or load at that joint. Suitably, the motors are arranged proximally of the joints whose motion they drive, so as to improve weight distribution. For clarity, only some of the motors and sensors are shown in FIG. 3. The arm may be generally as described in our co-pending patent application PCT/GB2014/053523.

Controllers for the motors, torque sensors and encoders are distributed within the robot arm. The controllers are connected via a communication bus to a control unit 309. The control unit 309 comprises a processor 310 and a memory 311. The memory 311 stores in a non-transient way software that is executable by the processor to control the operation of the motors 307 to cause the arm 300 to operate in the manner described herein. In particular, the software can control the processor 310 to cause the motors (for example via distributed controllers) to drive in dependence on inputs from the sensors 308 and from a surgeon command interface 312. The control unit 309 is coupled to the motors 307 for driving them in accordance with outputs generated by execution of the software. The control unit 309 is coupled to the sensors 308 for receiving sensed input from the sensors, and to the command interface 312 for receiving input from it. The respective couplings may, for example, each be electrical or optical cables, and/or may be provided by a wireless connection. The command interface 312 comprises one or more input devices whereby a user can request motion of the end effector in a desired way. The input devices could, for example, be manually operable mechanical input devices such as control handles or joysticks, or contactless input devices such as optical gesture sensors. The software stored in the memory 311 is configured to respond to those inputs and cause the joints of the arm and instrument to move accordingly, in compliance with a pre-determined control strategy. The control strategy may include safety features which moderate the motion of the arm and instrument in response to command inputs. Thus, in summary, a surgeon at the command interface 312 can control the instrument 306 to move in such a way as to perform a desired surgical procedure. The control unit 309 and/or the command interface 312 may be remote from the arm 300.

The illustrated surgical robot comprises a single robot arm. Other surgical robot systems may comprise a plurality of surgical robots and/or a plurality of robot arms. For example, other example surgical robot systems may comprise a surgical robot with a plurality of robot arms that can each receive and manipulate a surgical instrument, or they may comprise a plurality of surgical robots that each have a robot arm that can receive and manipulate a surgical instrument.

For ease of reference, the joints of the arm illustrated in FIG. 3 can be labelled as J1 (303a), J2 (303b), J3 (303c), J4 (303d), J5 (303e), J6 (303f), J7 (303g) and J8 (303h). Joint J4 can be considered as an "elbow" of the illustrated arm. The kinematics of this arm arrangement permit the elbow joint to move within a known and variable "nullspace" whilst keeping the wrist of the arm (the intersection of the axes of rotation of joints J6 and J7 in the illustrated example), which couples to the attachment for the instrument, at a desired position. The desired position is derived from the commanded position, as commanded by the command interface, taking into account the common joint velocity limit applied to multiple joints of the arm. Constraints applied to adjust movement and/or position of the arm can help ensure that the elbow is in the optimum location within that nullspace in order to perform any given task within a user-specified operating mode. Where movement of a joint of the arm might otherwise cause the common joint velocity limit to be exceeded, the elbow joint can move to compensate for this, which in some instances can avoid the motion of the wrist being affected (e.g. slowed down) whilst still complying with the common joint velocity limit.

A specific example of the present approach will now be described. This example refers to a surgical robot arm of the type illustrated in FIG. 3. In one example the robot arm comprises 8 joints. The first four joints from the base (J1 to J4), i.e. the four joints proximal to the base, enable a more distal portion of the arm to be positioned in 3D Cartesian space along the three orthogonal axes of that space. The joints may be the following type of joints: J1 (roll joint); J2 (pitch joint); J3 (roll joint); J4 (pitch joint). Subsequent joints, in this example the fifth to the eighth joints (J5 to J8) enable the portion of the arm distal of the fourth joint to be angularly rotated about that position. These subsequent joints may be the following type of joints: J5 (roll joint); J6 (pitch joint); J7 (yaw joint); J8 (roll joint). Thus, in this example, joints J1 to J4 are sufficient to define the position in Cartesian space of the distal portion of the arm. The distal portion of the arm can comprise joints J5 to J8.

Each of joints J1 to J4 has a respective minimum joint rotational position and a respective maximum joint rotational position. These minimum joint rotational positions and maximum joint rotational positions can be physical end points, i.e. angles past which the joint is not physically able to rotate, or they can be angles that are selected, for example in software control. Each of the joints is rotatable between its minimum joint rotational position and its maximum joint rotational position. In this example J1 is rotatable between –720 degrees and 720 degrees. J2 is rotatable between –90 degrees and 135 degrees. J3 is rotatable between –720 degrees and 720 degrees. J4 is rotatable between –5 degrees and 180 degrees. The difference between the minimum joint rotational position and the maximum joint rotational position in respect of J1 and/or J3 is suitably greater than the difference between the minimum joint rotational position and the maximum joint rotational position in respect of J2 and/or J4. This can be the case where, for example, J1 and/or J3 tend to move less than J2 and/or J4 during operation of the arm.

Each of joints J5 to J8 has a respective minimum joint rotational position and a respective maximum joint rotational position. These minimum joint rotational positions and maximum joint rotational positions can be physical end points, i.e. angles past which the joint is not physically able to rotate, or they can be angles that are selected, for example in software control. Each of the joints is rotatable between its minimum joint rotational position and its maximum joint rotational position. In this example J5 is rotatable between –720 degrees and 720 degrees. J6 is rotatable between –20 degrees and 23 degrees. J7 is rotatable between –120 degrees and 120 degrees. J8 is rotatable between –360 degrees and 360 degrees.

Knowledge of the joint states of each of the four joints J1 to J4 enables a permitted range of motion for each joint to be determined. For example, the joint states can comprise or indicate a joint angle within the range of joint angles at which a particular joint is currently located. For instance, the state of joint J2 may indicate that J2 is at a current angular position of 125 degrees. The permitted range of motion of J2 can be found by comparing the current angular position (125 degrees) with the minimum and maximum angular positions: –90 degrees and 135 degrees, respectively. Here the permitted range of motion includes a range of (–90-125) degrees in one direction and (135-125) degrees in the other direction. Thus the permitted range of motion of J1 in this example is 215 degrees one way, and 10 degrees the other way. Similar calculations can be performed for each of the other joints J1, J3 and J4. This will lead to the calculation of a permitted range of motion in respect of each of these four joints, i.e. J1 to J4. Since the techniques herein consider the case where joint velocity reaches zero by the joint rotation end point, it is only necessary to consider the permitted range of motion that is smaller, i.e. 10 degrees in the above example. Thus the determined permitted range of motion is suitably the range of motion to the closest end point of rotation from the current joint angular position. Where the joint is at its mid-point of rotation, then the range of motion will be the same in either direction. In this case that range is taken to be the permitted range of motion for that joint.

Each of joints J1 to J4 has a respective maximum velocity. These maximum velocities can be physical velocities, i.e. velocities which cannot physically be exceeded by the joints, or they can be velocities that are selected, for example in software control. In this example J1 is rotatable at up to 3 radians/second. J2 is rotatable at up to 3 radians/second. J3 is rotatable at up to 3 radians/second. J4 is rotatable at up to 3 radians/second. The maximum velocities of these joints need not be the same.

Each of joints J1 to J4 has a respective maximum acceleration (or deceleration). These maximum decelerations can be physical decelerations, i.e. decelerations which cannot physically be exceeded by the joints, or they can be decelerations that are selected, for example in software control.

The change in velocity of each of the joints can be up to the maximum deceleration. In this example J2 has a maximum deceleration of 5 radians/second^2. J4 has a maximum deceleration of 5 radians/second^2. The maximum decelerations of J1 and/or J3 can be set higher than the maximum decelerations of joints J2 and/or J4, for example, where J1 and/or J3 tend to move less than J2 and/or J4 during operation of the arm. In some cases the maximum decelerations of J1 and/or J3 can be set high enough that these decelerations are unlikely to be reached in practice, for example decelerations over 1000 radians/second^2. The maximum deceleration of J1 need not be the same as the maximum deceleration of J3. The maximum decelerations of J2 and J4 need not be the same.

Suitably the joint angles can be determined in radians, or converted to radians, or the velocities and decelerations can be determined in or converted to degrees. The unit used is not critical, but it will be understood that the same unit will be used in a consistent manner for the calculations.

A joint velocity limit is derived from the determined permitted range of motion. The joint velocity limit for a given joint is suitably derived using the permitted range of motion for that joint and the maximum deceleration for that joint. The joint velocity limit can be the highest velocity at which the joint can rotate whilst still being able to slow down and stop (at the maximum deceleration) by the joint rotational limit (i.e. within the permitted range of motion). For example, from the standard equations of motion, it can be found that the joint velocity limit is $$(2*(\text{permitted range of motion})*(\text{maximum deceleration}))^{(1/2)}.$$

Where the angle of any one of joints J1 to J4 is within a central portion of the range between the minimum joint angle and the maximum joint angle for that joint, the velocity limit for that joint can be determined to be the maximum velocity. For example, where the joint angle for a given joint is at a mid-point of its range, there may be no need to limit the joint velocity to be lower than the maximum velocity. This is because, when the joint angle is in this mid-point, the joint velocity limit that would be derived from the permitted range of motion and the maximum deceleration may be greater than the maximum velocity for that joint.

Thus, suitably a comparison is made between the maximum velocity for a given joint and the joint velocity limit as calculated for that joint. The smaller of these values is used as a limiting velocity for that joint.

For a particular maximum velocity and maximum deceleration, the permitted range of motion at which the joint velocity limit exceeds the maximum velocity can be determined. This permitted range of motion can be selected as a threshold value. It may only be necessary to calculate the joint velocity limit for that joint where the permitted range of motion for that joint falls below this threshold value. Where the permitted range of motion meets or exceeds this threshold value, the maximum velocity for that joint can be used as a limiting velocity for that joint. This approach can reduce the processing overhead in deriving the joint velocity limit. The threshold value is likely to differ between joints, due to differing joint characteristics, such as joint maximum decelerations and/or minimum and/or maximum joint rotational positions. The threshold values need not be different. Where the joint characteristics for given joints are the same, the threshold values for those joints can be the same.

Performing these calculations for each of joints J1 to J4 will result in four joint velocity limits—one for each joint.

In the present techniques, the most critical of these, e.g. the minimum joint velocity limit is considered. Thus, the minimum of the four joint velocity limits is selected to be a common joint velocity limit. The common joint velocity limit is a limit that can be applied to each of the four joints, J1 to J4, individually. The common joint velocity limit can be applied to a joint more distal from joint J4, for example the wrist (i.e. J6/J7 intersection). Applying the common joint velocity limit to this more distal joint can cause the velocity of joints J1 to J4 to be limited.

The common joint velocity limit can be selected based on the angular joint velocity limits. In some cases the common joint velocity limit can be selected in dependence on a transformation into Cartesian space of the angular joint velocity limits. The common joint velocity limit can be applied to the more distal joint by transforming the common joint velocity limit into Cartesian space and using the common joint velocity limit, as transformed, to limit the positional velocity in Cartesian space of that more distal joint. For example, a Jacobian matrix can be determined based on the joint angles of the joints of the arm. In this case, only the joint angles of joints J1 to J4 need be considered. Joint angles of the remaining joints (J5 to J8) need not be considered. Thus the joint angles of the joints distal of J4 can be set to zero when calculating the Jacobian matrix.

An inverse matrix can be calculated from the Jacobian matrix. The Euclidean norm for each row can be derived from the inverse matrix. This can provide unit vectors along each of the Cartesian x, y and z axes for each of joints J1 to J4. The inverse matrix can translate joint angle positions and joint velocities into joint positions and joint velocities in Cartesian space.

Thus, velocities in Cartesian coordinates can be calculated for each joint J1 to J4. The minimum of these velocities in Cartesian coordinates can be selected to be the common joint velocity limit.

The common velocity limit is used to limit the velocity of a plurality of joints of the arm. For example, the common joint velocity limit is used to limit the velocity of more than one of the four joints J1 to J4, for example each of joints J1 to J4 individually. To take an example, separate joint velocity limits for each of the joints J1 to J4 may be calculated to be $J1_{vel\text{-}limit}$, $J2_{vel\text{-}limit}$, $J3_{vel\text{-}limit}$ and $J4_{vel\text{-}limit}$. In this example, $J4_{vel\text{-}limit}$ is smaller than any of $J1_{vel\text{-}limit}$, $J2_{vel\text{-}limit}$ and $J3_{vel\text{-}limit}$. Thus, $J4_{vel\text{-}limit}$ is selected to be the common joint velocity limit. The velocity of each of J1, J2, J3 and J4 is limited to $J4_{vel\text{-}limit}$. Additionally or alternatively, the common joint velocity limit can be applied to the multiple joints by limiting the positional velocity in Cartesian space of the wrist to $J4_{vel\text{-}limit}$.

This common joint velocity limit can be applied in any suitable way. For example, the common joint velocity limit can be passed to the kinematics controller, which can take this common joint velocity limit into account when determining the desired pose of the arm in response to the commanded pose. The kinematics controller can use the common joint velocity limit to limit the velocity of each of joints J1 to J4 individually. For instance, the kinematics controller can use the common joint velocity limit, as applied to the position of the wrist (i.e. the position at which the axes of J6 and J7 intersect), when calculating the velocities of multiple joints of the arm. Limiting the positional velocity of the wrist can cause limits to be placed on the velocities of the individual joints J1 to J4. Where the common joint velocity limit is applied to the wrist, the kinematics controller can calculate desired joint movements of joints proximal of the wrist such that the velocity of the wrist does not exceed the common joint velocity limit. In doing so, the kinematics controller can effectively limit the joint velocities of each of the joints proximal of the wrist using the common joint velocity limit.

The kinematics controller can use the common joint velocity limit, as applied individually to joints J1 to J4, when calculating the velocities of multiple joints of the arm. Where the common joint velocity limit is applied to J1 to J4 individually, the kinematics controller can take this into consideration when calculating joint movements, including joint velocities, of other joints of the arm. Thus, where the arm can move from a first configuration to a second configuration in more than one way, as is likely to be the case for a redundant arm, the kinematics controller can calculate joint movements that attempt to keep the velocities of the individual joints below the common joint velocity limit. Where this is not possible, the kinematics controller can 'cap' the velocity of the joints at the common joint velocity limit, so that this limit is not exceeded.

There may be cases in which motion of a first joint will cause the wrist to move in, say, the positive x-direction, and motion of a second joint will cause the wrist to move in, say, the negative x-direction. Thus the velocity of movement of the wrist may be lower than the velocity of movement of the first joint. In such cases, the kinematics controller can calculate the desired movements of the joint in a way that permits the common joint velocity limit to be exceeded by the first joint whilst the velocity of the wrist is still limited to the common joint velocity limit. Thus it can be sufficient for the velocity of the wrist (or more generally, a portion of the arm distal of the multiple joints) to be limited to the common joint velocity limit. The velocity of the multiple joints individually need not also be directly limited to the common joint velocity limit. However, in practice it can be desirable to limit the velocity of the multiple joints individually to the common joint velocity limit. For example, the velocity of each of the multiple joints can be limited by the common joint velocity limit such that the velocities of each of the multiple joints individually does not exceed the common joint velocity limit.

In some implementations, for example where the velocities of the individual joints are limited to the common joint velocity limit, it is possible to apply a scaling factor so as to cause the positional velocity of the wrist (or more generally, a more distal portion of the arm from the multiple joints) to be limited to the common joint velocity limit. The scaling factor can, in some instances, be derived from the common joint velocity limit and the commanded wrist velocity, for example a ratio:

$$\frac{\text{common joint velocity limit}}{\text{commanded wrist velocity}}$$

This ratio can be applied to the velocity limit of each of the joints J1 to J4 individually, e.g. the ratio can be applied to the common joint velocity limit. This approach can help ensure that the velocity of the wrist does not exceed the common joint velocity limit.

Limiting the joint velocities in this way is likely to mean that there will be a difference between the commanded joint velocities and the actual joint velocities of the arm joints. Suitably, there is no 'catch-up' of the commanded movement which is in excess of the actual movement. That is, once the commanded joint velocities drop below the common joint velocity, the joints of the arm will be controlled to move at the new commanded joint velocities. Any commanded movement above the common joint velocity limit can be treated as 'lost' movement. This approach can help ensure that a user of the surgical robotic system is aware at all times of the extent of movement of the arm joints in response to commanded movement at the input controller. This approach helps ensure that there is no 'overshoot' of the joints of the arm beyond that expected by the user. Thus the present techniques can assist with the safe execution of control of the robot arm.

In the above discussion, joint velocities for all four of joints J1 to J4 are calculated, and the minimum of these joint velocities selected as the common joint velocity. In an alternative, once the permitted range of motion of each joint has been determined, the minimum of these permitted ranges of motion can be selected and can be used, together with the maximum deceleration for the relevant joint (i.e. the joint at the angular position with the minimum permitted range of motion) to derive the common joint velocity. There is no need in this case to calculate the joint velocity for any other joint. Thus a processing saving can be made, which can assist in increasing the efficiency of the control of the arm. This approach can be useful where the ratings or characteristics of the joints are the same. For example, where each of the joints under consideration, for example joints J1 to J4, have the same maximum deceleration. This approach may be useful where each of the joints has the same maximum velocity.

In the techniques discussed herein, the common joint velocity limit can usefully be obtained based on the measured joint angles. There is no need for additional data, for example commanded joint positions or a commanded pose to be considered when obtaining the common joint velocity limit.

In the example discussed here, the joint angles of joints J1 to J4 are sufficient to define the position of joint J4, and can also be sufficient to define the position of a joint distal of J4. For example, a wrist joint can be defined by the intersection of the axes of J6 and J7. The position of the wrist joint can suitably be defined by the angles of J1 to J4 only. Thus, only J1 to J4 need be considered when limiting the positional velocity of the wrist joint. Here, the positional velocity can be considered to be the velocity along the three orthogonal axes of Cartesian space.

It is also possible to limit the angular velocity of a joint distal of J4, for example the wrist joint. One way that this can be achieved is to consider a second Jacobian matrix (and inverse matrix, as described above with reference to deriving the common joint velocity limit) based on the joint angles of joints distal of J4, for example J5 to J7. The joint angle of J8 may also be taken into account, as desired.

The approach taken to calculate a further common joint velocity limit (or a common joint angular velocity limit) can be the same as described herein with respect to calculating the common joint velocity limit, where joints J5 to J7 are considered in place of joints J1 to J4. Where the further common joint velocity is applied to joints J5 to J7 individually, the scaling factor may be applied in a similar manner to that described elsewhere herein with reference to joints J1 to J4.

In an alternative, rather than determining two Jacobian matrices (one for J1 to J4 and the other for J5 to J7), a single Jacobian matrix can be determined based on J1 to J7. Thus positional and angular mappings can be considered at once. It is noted that this 'larger' Jacobian matrix based on J1 to J7 can be determined in addition to determining the 'smaller' Jacobian matrix based on J1 to J4. This may, however, lead to some duplication of processing effort.

One or more of the minimum joint rotational position, the maximum joint rotational position, the joint maximum velocity and the joint maximum deceleration can be determined in dependence on at least one of the following:
- a characteristic of the arm;
- an instrument to be attached to the arm;
- an environment of the arm;
- a procedure that the arm is used (or is to be used) to perform; and
- usage data gathered from system telemetry.

Figure 4:
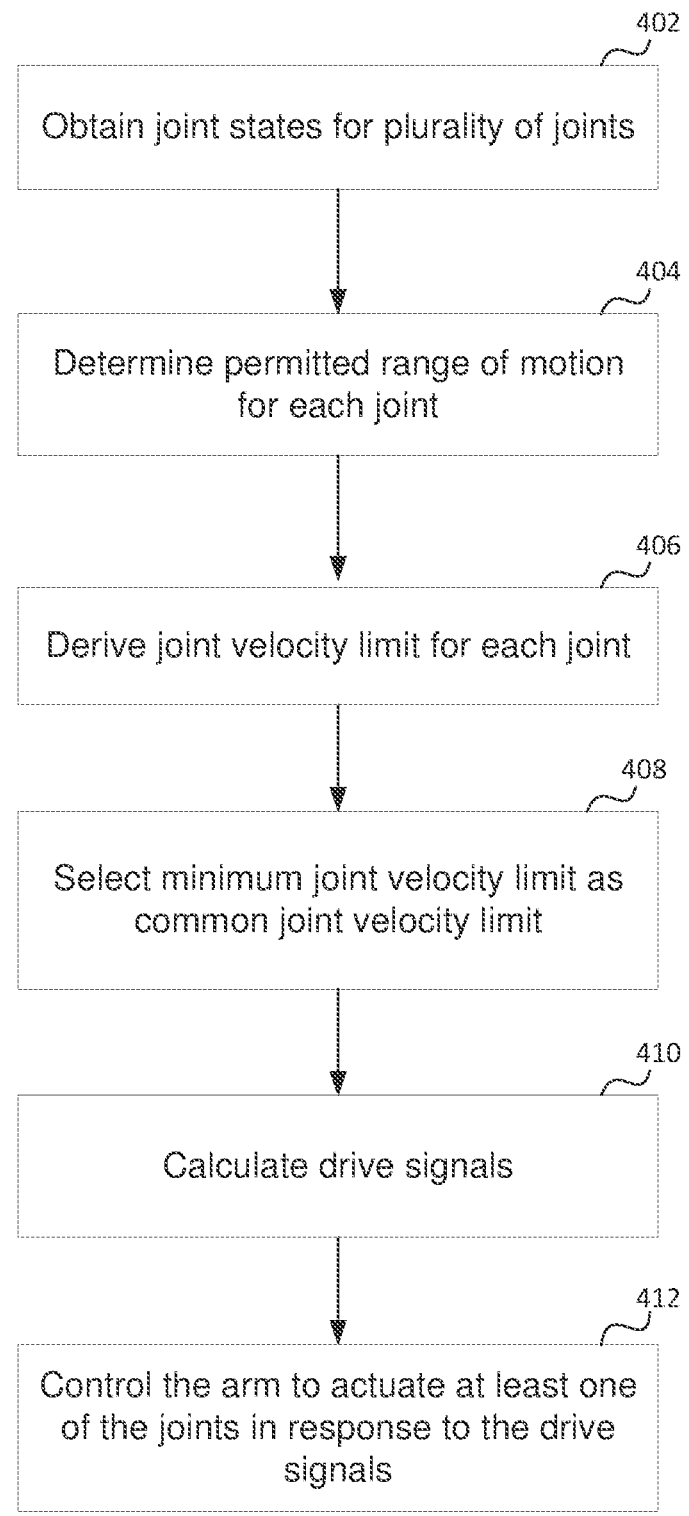
FIG. 4 illustrates a method of limiting joint velocity of a plurality of joints of a robotic system.

A method of limiting joint velocity of a plurality of joints of a robotic system such as a surgical robotic system will now be described with reference to FIG. 4. Joint states for a plurality of joints are obtained (402). For example, for a robot arm comprising n joints, joint states of k joints can be obtained, where k≤n. A permitted range of motion is determined for each joint (404), i.e. for each of the k joints. A joint velocity limit is derived for each joint (406), i.e. for each of the k joints. The minimum joint velocity limit is selected as a common joint velocity limit (408). The common joint velocity limit can then be used to calculate drive signals (410) for driving joints of the arm, for example at least the k joints. The arm is then controlled to actuate at least one of the joints in response to the drive signals (412).

Figure 5:
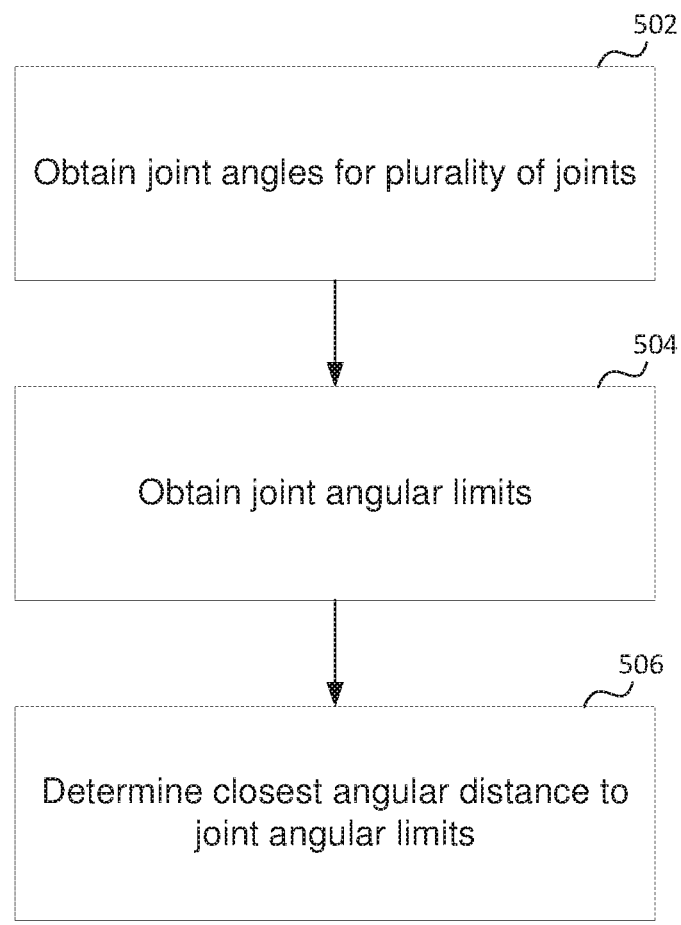
FIG. 5 illustrates a method of determining permitted ranges of motion of joints.

FIG. 5 illustrates a method of determining permitted ranges of motion of joints. Joint angles for a plurality of joints are obtained (502). The plurality of joints is suitably the k joints discussed in the context of FIG. 4. Joint angular limits are obtained for each of the joints (504). The joint angular limits can be obtained from any suitable source, for example a memory. For each joint, closest angular distances are determined to the joint angular limit (506). This can be determined by calculating the angular distance between the current joint angle and both of the minimum and maximum joint angles, and taking the smaller of the resulting values. This closest angular distance can be used as the permitted range of motion of that joint.

Figure 6:
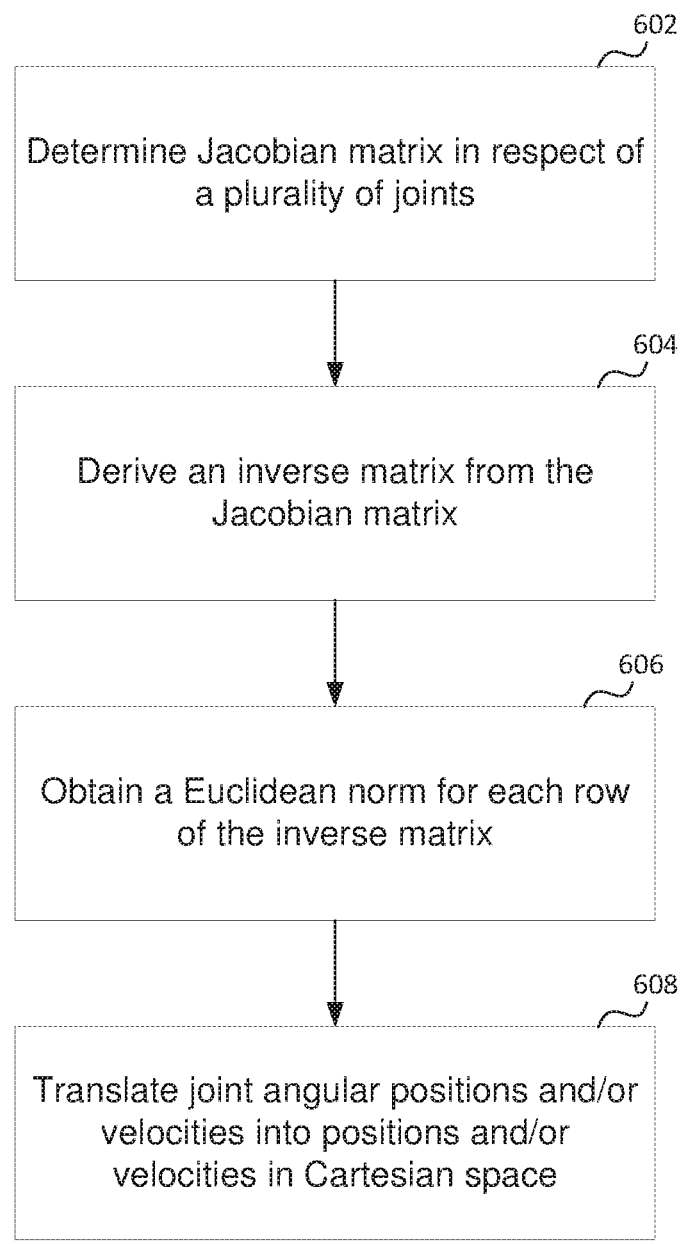
FIG. 6 illustrates a method of translating joint angle positions and/or joint velocities into Cartesian space.

FIG. 6 illustrates a method of translating joint angle positions and/or joint velocities into Cartesian space. At 602 a Jacobian matrix is determined in respect of a plurality of joints. The Jacobian matrix can be determined in respect of a subset of arm joints (i.e. k joints) or all of the joints of the arm (i.e. n joints). At 604 an inverse matrix is derived from the Jacobian matrix. A Euclidean norm is obtained in respect of each row of the inverse matrix (606). It may be sufficient in some examples to obtain the Euclidean norm for a subset of the rows of the inverse matrix, but preferably the Euclidean norm is obtained for each row. At 608 joint angular positions and/or velocities are translated into Cartesian space. This translation suitably makes use of the inverse matrix derived at 604 and the Euclidean norms obtained at 606.

Figure 7:
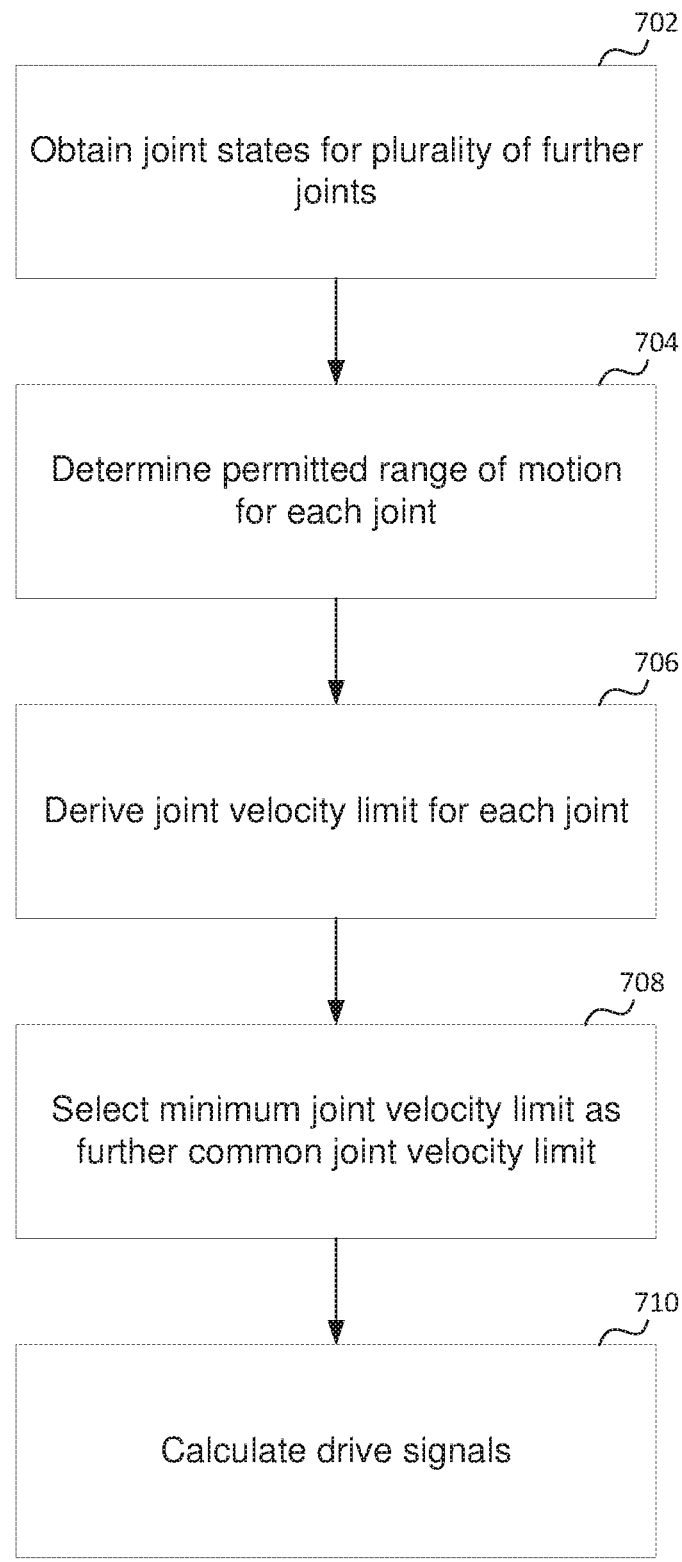
FIG. 7 illustrates a method of limiting joint angular velocity of a plurality of further joints of a robotic system.

FIG. 7 illustrates a method of limiting joint angular velocity of a plurality of joints of a robotic system such as a surgical robotic system. Joint states for a plurality of further joints are obtained (702). For example, for a robot arm comprising n joints, joint states of (n−k) joints can be obtained, where k<n. A permitted range of motion is determined for each joint of the plurality of further joints (704), i.e. for each of the (n−k) joints. A joint velocity limit is derived for each of the plurality of further joints (706), i.e. for each of the (n−k) joints. The minimum joint velocity limit is selected as a further common joint velocity limit (708). The further common joint velocity limit can then be used to calculate drive signals (710) for driving joints of the arm, for example at least the (n−k) joints.

Figure 8:
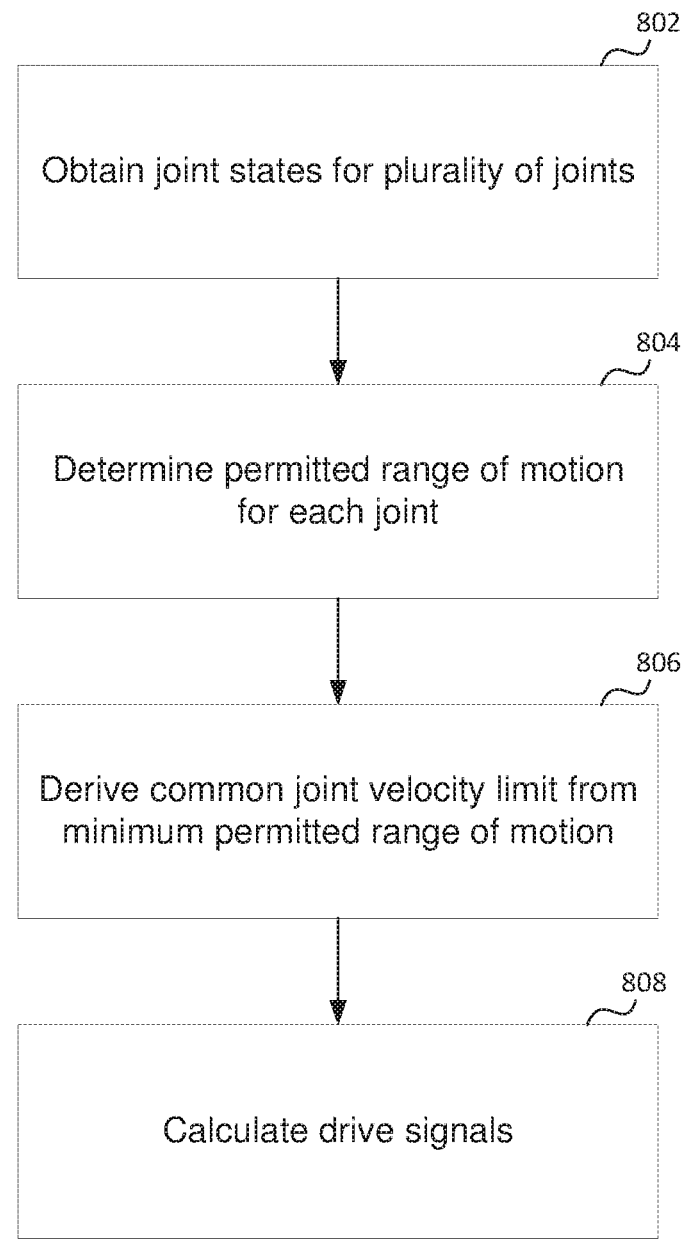
FIG. 8 illustrates another method of limiting joint velocity of a plurality of joints of a robotic system.

FIG. 8 illustrates another method of limiting joint velocity of a plurality of joints of a robotic system such as a surgical robotic system. Joint states for a plurality of joints are obtained (802). For example, for a robot arm comprising n joints, joint states of k joints can be obtained, where k≤n. A permitted range of motion is determined for each joint (804), i.e. for each of the k joints. A common joint velocity limit is derived from the minimum permitted range of motion for the k joints (806). The common joint velocity limit can then be used to calculate drive signals (808) for driving joints of the arm, for example at least the k joints.

Figure 9:
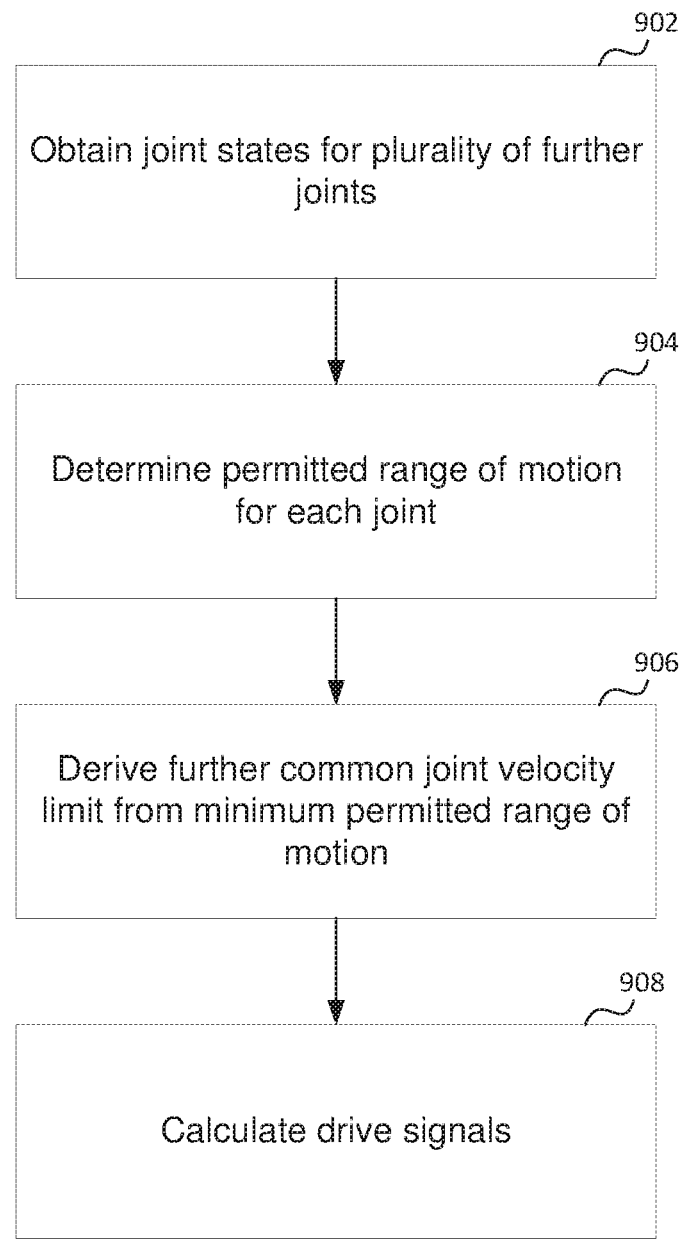
FIG. 9 illustrates another method of limiting joint angular velocity of a plurality of further joints of a robotic system.

FIG. 9 illustrates another method of limiting joint angular velocity of a plurality of joints of a robotic system such as a surgical robotic system. Joint states for a plurality of further joints are obtained (902). For example, for a robot arm comprising n joints, joint states of (n−k) joints can be obtained, where k<n. A permitted range of motion is determined for each joint of the plurality of further joints (904), i.e. for each of the (n−k) joints. A further common joint velocity limit is derived from the minimum permitted range of motion for the (n−k) joints (906). The further common joint velocity limit can then be used to calculate drive signals (908) for driving joints of the arm, for example at least the (n−k) joints.

In some cases the joint states can be obtained from a position of one or more joints of the arm, for example a distal arm joint. The joint states may be obtained in dependence on the position of the wrist joint. The joint states can be obtained from a position commanded by an input controller at a surgeon console. Where joint states are obtained at a known sampling rate, the velocity of the joints and/or of a portion of the arm, can be determined from sampled positions.

The robot arm comprises n joints. Joint states of k joints can be obtained (where k<n). Suitably the k joints are the k most proximal joints of the arm, i.e. J1-Jk. The joint states suitably comprise joint angles. The joint angles can be represented as a vector, for example, where k=4

$$q=[q_1,q_2,q_3,q_4]$$

If required, zeros can be appended to q in respect of the remaining joints. So, where there are 8 joints (J1-J8), q can be written as $$q=[q_1,q_2,q_3,q_4,0,0,0,0]$$

Not all of the joints of the arm need be considered. Thus, where there are 8 joints it can be sufficient to consider the 7 most proximal joints. In this case q can be written as $$q=[q_1,q_2,q_3,q_4,0,0,0]$$

It is convenient to obtain from the arm or from an arm control system joint states, such as joint angles, of all n joints at once. These angles can conveniently be stored locally. The angles of the k joints may then be accessed.

As mentioned, the robot arm can be controlled by a user-manipulatable input controller. In some cases, feedback, such as haptic feedback, can be provided to a user of the system. The feedback can be provided through the input controller. For example, the input controller can vibrate when the common joint velocity limit and/or the further common joint velocity limit is reached. The nature of the feedback can differ between the common joint velocity limit being reached and the further common joint velocity limit being reached.

The system may be configured to provide a resistive force to movement of the input controller that would cause motion of the arm to exceed the common joint velocity limit and/or the further common joint velocity limit. In this way, a user of the system can be made aware of the 'lost' movement, i.e. movement of the input controller that will not result in further or faster movement of one or more joints of the robot arm.

Feedback may be provided in any convenient manner, for example by the emission of an audio-visual signal. The audio-visual signal may comprise a light. The audio-visual signal may comprise a sound. The audio-visual signal may comprise lights with differing colours, intensities, continuous and/or flashing patterns, and so on. The audio-visual signal may comprise a sound with differing tone, volume, message and so on. Suitably the system comprises one or more lights configured to output the visual element of the audio-visual signal. Suitably the system comprises one or more speakers configured to output the audible element of the audio-visual signal.

The light and/or speaker can be provided at any convenient location on the system, for example on a user console, on the input controller, on the robot arm and so on.

The audio-visual signal may be emitted together with or instead of the provision of the haptic feedback.

In the description above actions taken by the system have been split into functional blocks or modules for ease of explanation. In practice, two or more of these blocks could be architecturally combined. The functions could also be split into different functional blocks.

The present techniques have been described in the context of surgical robotic systems, though the features described below are not limited to such systems, but may be applied to robotic systems more generally. In some examples, the present techniques may be applied to robotic systems that operate remotely. Some examples of situations in which the present techniques may be useful include those that make use of 'snake-like' robots for exploration, investigation or repair. In the case of a surgical robot the end effector could be a surgical tool such as a scalpel, surgical cutter, surgical pincer or cauteriser.

Robotic systems can include manufacturing systems, such as vehicle manufacturing systems, parts handling systems, laboratory systems, and manipulators such as for hazardous materials or surgical manipulators.

The joints could be driven by electric motors, which could be rotary or linear, or by other means such as hydraulic or pneumatic actuators. These would be driven from the same control algorithms.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

What is claimed is:

1. A method for limiting joint velocity of a plurality of joints of a surgical robotic system, the surgical robotic system comprising a robot having a base and an arm extending from the base to an attachment for an instrument, the arm comprising a plurality of joints whereby the configuration of the arm can be altered, the method comprising:
   obtaining joint states for a first group of k joints of the arm, where k>1; and
   for each of the k joints:
      determining from the obtained joint state a permitted range of motion for that joint;
      deriving, using the permitted range of motion, a joint velocity limit for that joint;
      selecting the minimum joint velocity limit of the k joints to be a common joint velocity limit used to limit each of the k joints individually;
      calculating drive signals for driving the k joints to actuate at least one of the k joints wherein the velocity of each of the k joints is limited using the common joint velocity limit; and
      controlling the arm to actuate at least one of the k joints in response to the drive signals.

2. A method according to claim 1, in which the first group of k joints comprises k joints proximal to the base of the arm, and the common joint velocity limit limits the positional velocity of the kth joint along orthogonal directions in Cartesian space.

3. A method according to claim 1, in which the first group of k joints comprises k joints proximal to the base of the arm, and the k joints enable a position of a (k+m)th joint to be uniquely determined, where m>0.

4. A method according to claim 1, in which the common joint velocity limit limits the positional velocity of a (k+m)th joint along orthogonal directions in Cartesian space.

5. A method according to claim 1, in which the velocity of each of the k joints individually is limited to the common joint velocity limit.

6. A method according to claim 1, in which the arm comprises n joints, where n>k, and the method comprises:
   obtaining joint states for a second group of (n−k) joints of the arm;
   for each of the (n−k) joints:
      determining from the obtained joint state a permitted range of motion for that joint;
      deriving, using the permitted range of motion, a joint velocity limit for that joint;
      selecting the minimum joint velocity limit of the (n−k) joints to be a further common joint velocity limit for each of the (n−k) joints individually; and
      calculating drive signals for driving the (n−k) joints wherein the velocity of each of the (n−k) joints is limited to the further common joint velocity limit.

7. A method according to claim 1, in which obtaining joint states for one or both of the first group of k joints and the second group of (n−k) joints comprises obtaining joint angles.

8. A method according to claim 1, in which determining the permitted range of motion of a joint comprises determining a closest angular distance to a joint angular limit for that joint.

9. A method according to claim 8, in which deriving the joint velocity limit comprises using a maximum deceleration for the respective joint and the determined closest angular distance to the joint angular limit.

10. A method according to claim 6, in which the further common joint velocity limit limits the angular velocity of a (k+m)th joint, where m>0.

11. A method according to claim 8, in which at least one of the joint angular limit for a joint and the maximum deceleration for a joint comprises a predetermined value and/or is determined from a physical characteristic of the joint, and/or is user-definable.

12. A method according to claim 8, in which where the determined closest angular distance to the joint angular limit exceeds a threshold angular distance, the joint velocity limit for that joint comprises a predetermined joint velocity limit value.

13. A method according to claim 1, in which deriving the joint velocity limit comprises translating joint angular positions and/or velocities into positions and/or velocities, respectively, in Cartesian space.

14. A method according to claim 13, in which the translating comprises determining a Jacobian matrix.

15. A method according to claim 14, in which the translating comprises using the determined Jacobian matrix to derive an inverse matrix.

16. A method according to claim 15, in which the translating comprises determining a Euclidean norm in respect of each row of the inverse matrix.

17. A method according to claim 1, comprising providing feedback to a user of the surgical robotic system based on a commanded joint velocity for a joint exceeding the common joint velocity limit or further common joint velocity limit for that joint.

18. A method according to claim 17, in which the surgical robotic system comprises an input controller manipulatable by a user thereby to alter the configuration of the arm, and the method comprises providing haptic feedback via the input controller.

19. A joint velocity limiting system for limiting joint velocity of a plurality of joints of a surgical robotic system, the surgical robotic system comprising a robot having a base and an arm extending from the base to an attachment for an instrument, the arm comprising a plurality of joints whereby the configuration of the arm can be altered, the joint velocity limiting system being configured to:
   obtain joint states for a first group of k joints of the arm, where k>1; and
   for each of the k joints:
      determine from the obtained joint state a permitted range of motion for that joint;
      derive, using the permitted range of motion, a joint velocity limit for that joint;
      select the minimum joint velocity limit of the k joints to be a common joint velocity limit used to limit each of the k joints individually;
      calculate drive signals for driving the k joints to actuate at least one of the k joints wherein the velocity of each of the k joints is limited using the common joint velocity limit; and
      control the arm to actuate at least one of the k joints in response to the drive signals.

20. A non-transitory computer readable storage medium having stored thereon computer readable instructions that, when executed at a computer system, cause the computer system to perform a method for limiting joint velocity of a plurality of joints of a surgical robotic system, the surgical robotic system comprising a robot having a base and an arm extending from the base to an attachment for an instrument, the arm comprising a plurality of joints whereby the configuration of the arm can be altered, the method comprising:
   obtaining joint states for a first group of k joints of the arm, where k>1; and
   for each of the k joints:
      determining from the obtained joint state a permitted range of motion for that joint;
      deriving, using the permitted range of motion, a joint velocity limit for that joint;
      selecting the minimum joint velocity limit of the k joints to be a common joint velocity limit used to limit each of the k joints individually;
      calculating drive signals for driving the k joints to actuate at least one of the k joints wherein the velocity of each of the k joints is limited using the common joint velocity limit; and
      controlling the arm to actuate at least one of the k joints in response to the drive signals.

* * * * *